US010772491B2

(12) United States Patent
Chouinard et al.

(10) Patent No.: US 10,772,491 B2
(45) Date of Patent: Sep. 15, 2020

(54) APPARATUS FOR DECONTAMINATING EQUIPMENT HAVING INTERNAL CHANNELS (LUMENS)

(71) Applicant: STERIS INC., Temecula, CA (US)

(72) Inventors: Alain Chouinard, Quebec (CA); Louis Martineau, Levis (CA); Nicolas Verreault, Quebec (CA); Maxime Robert, L'Ancienne-Lorette (CA)

(73) Assignee: STERIS INC., Temecula, CA (US)

( * ) Notice: Subject to any disclaimer, the term of this patent is extended or adjusted under 35 U.S.C. 154(b) by 235 days.

(21) Appl. No.: 15/652,313

(22) Filed: Jul. 18, 2017

(65) Prior Publication Data

US 2018/0020905 A1 Jan. 25, 2018

Related U.S. Application Data

(60) Provisional application No. 62/365,615, filed on Jul. 22, 2016.

(51) Int. Cl.
*A61B 1/12* (2006.01)
*B08B 9/032* (2006.01)
*B08B 9/023* (2006.01)
*G01M 3/02* (2006.01)
(Continued)

(52) U.S. Cl.
CPC .......... *A61B 1/125* (2013.01); *A61B 1/00057* (2013.01); *A61B 1/00059* (2013.01);
(Continued)

(58) Field of Classification Search
CPC . A61B 1/125; A61B 1/00057; A61B 1/00059; A61B 1/123; A61L 2/24;
(Continued)

(56) References Cited

U.S. PATENT DOCUMENTS 5,279,799 A 1/1994 Moser ........................ 422/292
5,761,069 A 6/1998 Weber et al.
(Continued)

FOREIGN PATENT DOCUMENTS

EP 1779769 A2 5/2007
WO WO-2016/094979 A1 6/2016

OTHER PUBLICATIONS

International Search Report and Written Opinion issued in corresponding International Application No. PCT/US17/43074 dated Nov. 27, 2017.
(Continued)

*Primary Examiner* — Nadine G Norton
*Assistant Examiner* — Christopher Remavege
(74) *Attorney, Agent, or Firm* — Kusner & Jaffe (57) ABSTRACT

A method of cleaning an endoscope in a computer-controlled washer/disinfector comprising the steps of connecting each lumen of an endoscope to a fluid distribution system for selectively conveying pressurized air or pressurized fluids through lumens in an endoscope; identifying the type of endoscope to be cleaned in said washer/disinfector; determining a blockage threshold flow coefficient for each lumen for said endoscope to be cleaned; pressurizing each lumen in said endoscope individually and determining an actual flow coefficient through said lumen; determining whether said endoscope is suitable for cleaning by comparing said actual flow coefficients for a lumen in said endoscope to said blockage threshold flow coefficient for said lumen; and determining whether a connection to a lumen in said endoscope is properly connected based upon said flow coefficient through said lumen.

14 Claims, 7 Drawing Sheets

(51) Int. Cl.
*A61L 2/18* (2006.01)
*A61L 2/26* (2006.01)
*G01M 3/28* (2006.01)
*A61B 1/00* (2006.01)
*A61L 2/22* (2006.01)
*A61L 2/24* (2006.01)

(52) U.S. Cl.
CPC ............... *A61B 1/123* (2013.01); *A61L 2/18* (2013.01); *A61L 2/22* (2013.01); *A61L 2/24* (2013.01); *A61L 2/26* (2013.01); *B08B 9/023* (2013.01); *B08B 9/0323* (2013.01); *B08B 9/0325* (2013.01); *B08B 9/0328* (2013.01); *G01M 3/02* (2013.01); *G01M 3/2853* (2013.01); *A61L 2202/15* (2013.01); *A61L 2202/17* (2013.01); *A61L 2202/24* (2013.01)

(58) Field of Classification Search
CPC ..... A61L 2/22; A61L 2/26; A61L 2/18; A61L 2202/24; A61L 2202/15; A61L 2202/17; G01M 3/2853; G01M 3/02; B08B 9/0323; B08B 9/023; B08B 9/0325; B08B 9/0328
USPC ....... 134/102.2, 113, 166 R, 168 C, 170, 18, 134/56 R; 422/105, 292, 300, 905; 700/266; 600/118
See application file for complete search history.

(56) References Cited

U.S. PATENT DOCUMENTS

| | | | | |
|---|---|---|---|---|
| 6,068,815 A * | 5/2000 | Oberleitner | ............ | A01N 37/16 134/170 |
| 6,260,560 B1 * | 7/2001 | Walta | .................... | A61B 1/125 134/166 R |
| 7,340,943 B2 * | 3/2008 | Jackson | ............. | A61B 1/00057 73/49.2 |
| 7,479,257 B2 * | 1/2009 | Nguyen | .................... | A61L 2/28 422/119 |
| 7,686,761 B2 * | 3/2010 | Jackson | ............. | A61B 1/00057 600/155 |
| 7,901,349 B2 * | 3/2011 | Feld | .................... | A61B 1/00057 600/117 |
| 8,176,771 B2 * | 5/2012 | Onishi | ............... | A61B 1/00057 422/28 |
| 8,673,212 B2 * | 3/2014 | McDonnell | ............... | B08B 9/00 422/28 |
| 2006/0252991 A1 * | 11/2006 | Kubach | ............ | A61B 1/00057 600/118 |
| 2007/0193604 A1 * | 8/2007 | Weber | .................... | A61B 90/70 134/18 |
| 2009/0192354 A1 * | 7/2009 | Hasegawa | ............... | A61B 1/123 600/118 |
| 2009/0220377 A1 | 9/2009 | Hasegawa et al. | | |
| 2011/0290034 A1 * | 12/2011 | McDonnell | ........ | A61B 1/00057 73/756 |
| 2011/0296909 A1 * | 12/2011 | Eschborn | ........... | A61B 1/00057 73/198 |
| 2012/0253124 A1 * | 10/2012 | Torisawa | ............... | A61B 1/015 600/118 |
| 2014/0190520 A1 | 7/2014 | Noack | | |
| 2016/0081531 A1 * | 3/2016 | Yoshie | ............... | A61B 1/00057 73/40 |

OTHER PUBLICATIONS

Extended European Search Report issued in related/corresponding International Application No. PCT/US17/43074 dated Feb. 6, 2020.

* cited by examiner

APPARATUS FOR DECONTAMINATING EQUIPMENT HAVING INTERNAL CHANNELS (LUMENS)

FIELD OF INVENTION

The present invention relates generally to equipment for washing medical instruments and, more particularly, to a medical washer for washing medical equipment containing internal channels (lumens). The present invention is particularly applicable to cleaning endoscopes and will be described with particular reference thereto. Although it will be appreciated that the invention has further, broader applications to other types of medical devices containing internal channels (lumens).

BACKGROUND OF THE INVENTION

An endoscope is a long, slender, tubular optical instrument used as a viewing system for examining internal body parts, such as lungs, stomach, bladder and bowels. An endoscope may be a rigid or flexible tube, fitted with lenses, a fiber-optical light source and a variety of different medical instruments, such as probes, forceps, suction devices or other tools for examination or retrieval of tissue. In this respect, endoscopes include a plurality of elongated channels (lumens) that extend through the device. Once used within a patient, an endoscope must be cleaned and sterilized prior to subsequent use.

It is known to wash endoscopes in large medical washers that expose the exterior of the endoscope, as well as the internal channels, to cleaning solutions. U.S. Pat. No. 5,279,799 to MOSER discloses an apparatus for cleaning and testing endoscopes by injecting pressurized air and washing liquids into the channels (lumens) of the endoscope and monitoring the same. The MOSER patent discloses a washing chamber that is provided with retractable racks that hold the endoscopes during cleaning and testing. The racks include a connector for detachably connecting tubes and supplying the air and washing liquid to the endoscopes. A piston-driven manifold connects a plurality of inlet lines to the tubes connected to the endoscope.

A latter patent, namely, U.S. Pat. No. 8,673,212 to MCDONNELL et al., discloses an apparatus used to test for blockages and leaks in an endoscope. The apparatus insures that channels within the endoscope are unblocked and not leaking prior to cleaning, disinfecting and sterilization. The apparatus provides a means to pressurize and direct fluid to the passageways (lumens). The apparatus operates by exposing each channel to a pressurized gas. The flow value of the channel is compared to a value stored within an internal memory of a control unit. The stored value of air pressure and air flow is determined based upon the operating parameters of a known endoscope. Air flow is established through the duct, and a constant pressure value is maintained. A flow value is read and determined by the control unit and compared to the stored value. If the air flow value of the device is similar to the stored value, the duct is considered to be opened or clear. If the value is lower than the predetermined stored value, the duct is considered to be blocked. If blocked, the medical device is removed for maintenance to remove the blockage. If the air flow value is higher than the predetermined stored value, the latter indicates that there is not a proper air-tight connection between the medical device and the testing apparatus.

The present invention utilizes the testing device disclosed in the prior patent to monitor and control a cleaning process during the actual cleaning and washing of the medical device. Further, the present invention provides connection means between the testing device and the actual medical instrument, which is more reliable and simplifies the connection of the "air supply lines to the medical device."

SUMMARY OF THE INVENTION

In accordance with a first aspect of the present invention, there is provided a washer/disinfector for washing and disinfecting instruments. The washer is comprised of a housing defining a chamber. Spray arms are disposed in the chamber. The spray arms are for spraying a fluid in the chamber. A rack is dimensioned to be received within the chamber for holding medical instruments to be washed and disinfected. The rack is movable between a first position within the chamber and a second position extending from the chamber. An apparatus for testing and/or cleaning one or more channels or lumens in a medical instrument is provided. An elongated flexible connector, having one or more passageways extending therethrough, has a first end connectable to the apparatus and a second end connectable to a medical instrument in the rack. The connector is movable with the rack as the rack moves between the first position and the second position.

In accordance with another aspect of the present invention, there is provided a method for operating a computer-controlled washer/disinfector for cleaning a medical endoscope. The method comprises the steps of:
  storing in memory identification and operating characteristics for a plurality of clean endoscopes, the operating characteristics including flow characteristics for each lumen within an endoscope and a blockage threshold flow coefficient for each lumen within an endoscope;
  connecting each lumen of an endoscope to be cleaned to a fluid distribution system for selectively conveying pressurized air or pressurized fluids through lumens in an endoscope;
  identifying the type of endoscope to be cleaned in the washer/disinfector; determining the blockage threshold flow coefficient for each lumen for the endoscope to be cleaned;
  pressurizing each lumen in the endoscope individually and determining an actual flow coefficient through the lumen;
  determining whether the endoscope is suitable for cleaning by comparing the actual flow coefficients for a lumen in the endoscope to the blockage threshold flow coefficient for the lumen; and
  determining whether a connection to a lumen in the endoscope is properly connected based upon the flow coefficient through the lumen.

In accordance with another aspect of the present invention, there is provided a method of testing channels or lumens within an endoscope, comprising the steps of:
  connecting each individual lumen within an endoscope to a source of pressure;
  measuring the pressure and air flow through each individual lumen separately;
  determining a flow coefficient for each individual lumen based on the measured air pressure and the measured air flow;
  exposing each possible pair of lumens in the endoscope to the source of pressure;
  determining a flow coefficient for each possible pair of lumens in the endoscope based on a measured air flow at a measured pressure for the pair of lumens; and comparing the flow coefficient for a pair of lumens to a sum of the flow coefficients of the individual lumens forming the pair of lumens, wherein a flow coefficient for the pair of lumens that is less than the sum of the air flow coefficients of the individual lumens forming the pair is indicative of the pair of lumens merging into a single lumen within the endoscope.

An advantage of the present invention is a method of testing medical devices to determine whether two ducts within a device would merge into a single duct within the device.

Another advantage of the present invention is a system as described above, wherein establishing a minimum flow through a known duct allows operation of a cleaning cycle.

Another advantage of the present invention is a system as described above that allows for more efficient purging of fluids from a duct or passageway in a medical device through knowledge of the configuration of the duct as predetermined through an initial test and as confirmed during operation of the purging phase.

Another advantage of the present invention is a system as described above that tests each individual duct or passageway through a device alone and in combination of other ducts or passageways to determine the configuration of the passageways through the medical device.

A still further advantage of the present invention is a system as described above that, when pairs of ducts or passageways in a medical device merge into a single, larger duct, draining of such combination ducts (i.e., purging) is conducted simultaneously during a cleaning cycle.

Another advantage of the present invention is a washer/disinfector having fewer moving parts for connecting a fluid circulation system to the internal channels of a medical instrument to be cleaned.

Another advantage of the present invention is a washer/disinfector, as described above, wherein a rack for holding a medical instrument to be cleaned is always connected to a fluid circulation system.

A still further advantage of the present invention is a washer/disinfector, as described above, having a resilient flexible connector that is connectable at a first end to an apparatus for testing and cleaning medical instruments and is connectable at a second end to a medical instrument, which flexible connector is movable with a movable rack that is movable into and out of the washer/disinfector.

DETAILED DESCRIPTION OF PREFERRED EMBODIMENTS

Figure 1:
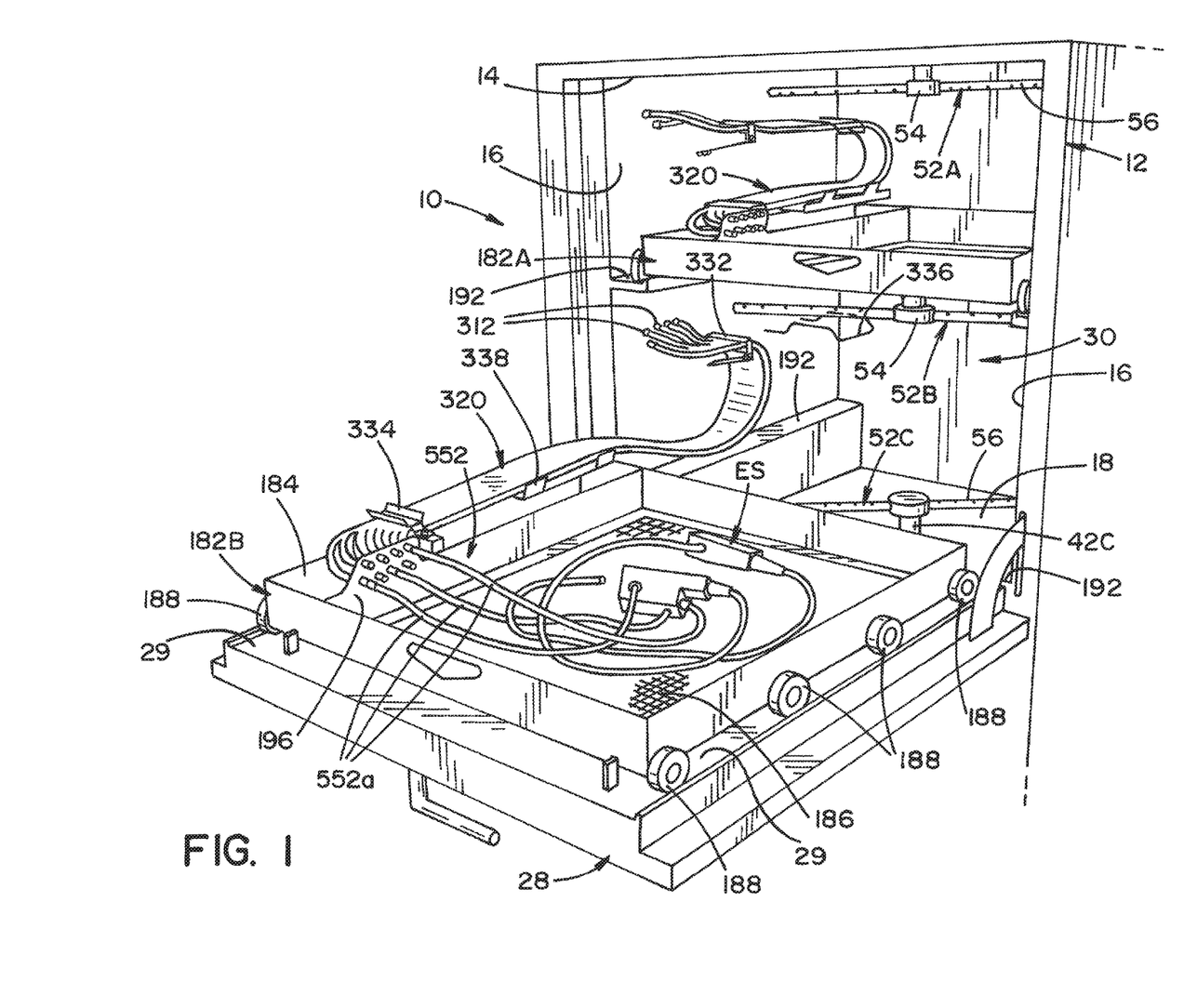
FIG. 1 is a front perspective view of a washing chamber of a washer/disinfector, showing a tray (a lower tray) removed from the washing chamber with an endoscope therein.

Referring now to the drawings wherein the showings are for the purpose of illustrating one embodiment of the invention only, and not for the purpose of limiting same, FIG. 1 shows a schematic view of a washer illustrating one embodiment of the present invention. In the embodiment shown, washer 10 is a washer designed for washing and decontaminating medical instruments and/or devices.

Washer 10 is generally comprised of a housing 12 that defines a washing chamber 30. Housing 12 is defined by an upper wall 14, side walls 16 and a bottom wall 18. Bottom watt 18 is formed to include a sloped sump 22 that is disposed at the bottom of housing 12. Sump 22 is provided to receive washing or rinsing fluids. A heating element 24 (schematically illustrated in FIG. 7) is disposed in sump 22 to selectively heat fluids therein. A door 28 in a front side wall defines an access opening to washing chamber 30.

A fluid circulation system 40 (schematically illustrated in FIG. 7) is provided to circulate fluids through washer 10 and washing chamber 30. Fluid circulation system 40 includes a circulation conduit 42 that fluidly connects sump 22 to first, second and third branch conduits 42A, 42B, 42C that have an upper, intermediate and lower spray arm assemblies 52A, 52B, 52C attached thereto, respectively. First branch conduit 42A extends through upper wall 14 of housing 12 and has an end disposed in an upper portion of washing chamber 30 with upper spray arm assembly 52A attached thereto. Second branch conduit 42B extends through a side wall 16 into a middle portion of washing chamber 30 with intermediate spray arm 52B attached to the end thereof. Third branch conduit 42C extends through bottom wall 18 of housing 12 and has an end disposed in a lower portion of washing chamber 30 with lower spray arm assembly 52C attached thereto. Spray arm assemblies 52A, 52B, 52C are essentially identical and as such only upper spray arm assembly wilt be described in detail. Each spray arm assembly 52A, 52B, 52C is comprised of a central hub 54 with arms 56 extending therefrom, as shown in FIG. 1. Central hub 54 defines an internal cavity (not shown) that is in fluid communication with an associated branch conduit 42A, 42B, 42C. Central hub 54 is rotatable mounted to an end of a branch conduit 42A, 42B, 42C. An elongated spray arm 56 defines an internal passage (not shown). Spray arm 56 is mounted to hub 54 with the internal passage therein in fluid communication with the internal cavity of central hub 54. A series of spray holes or orifices (not shown) are disposed in a wall of arms 56 at discrete locations.

A pump 62 is provided within circulation conduit 42 for pumping fluids from sump 22 to spray arm assemblies 52A, 52B, 52C. A motor 64 drives pump 62.

Figure 7:
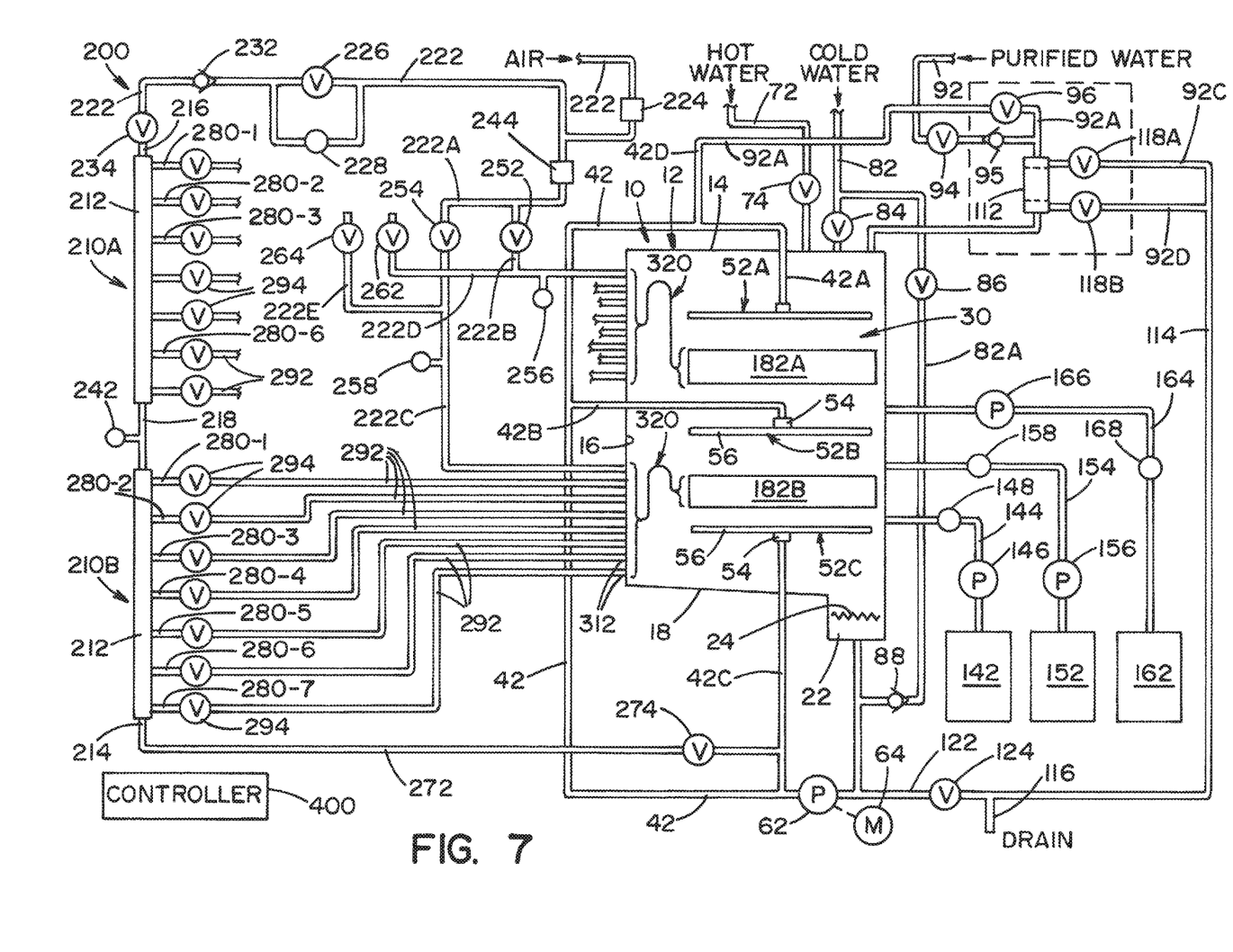
FIG. 7 is a schematic view showing a washer/disinfector and a testing apparatus for testing inner channels (lumen) within an endoscope to be cleaned within the washing chamber of the washer/disinfector.

As best seen in FIG. 7, a hot water line 72, a cold water line 82 and a purified water line 92 are connected to washer 10. Hot water line 72 is connected at one end to a source of hot water and at the other end to the top wall 14 of housing 12. A valve 74 disposed in hot water line 72 controls the flow of hot water therethrough. Similarly, cold water line 82 is connected at one end to a cold water source and at the other end to a top wall 14 of housing 12. A control valve 84 in cold water line 82 controls the flow of cold water from the cold water source to the washing chamber 30. A branch line 82A from cold water line 82 is connected to circulation conduit 42 between sump 22 and pump 62. A valve 86 within branch line 82A controls the flow of water therethrough. A directional check valve 88 is disposed within branch line 82A to prevent the flow from circulation conduit 42 to the branch line 82A. Purified water line 92 connects washer 10 to a source of purified water. A valve 94 within purified water line 92 controls flow therethrough. A first branch line 92A connects purified water line 92 to circulation conduit 42 and in turn to spray arm assembly 52A. A filter 112 is disposed within purified water line 92. A pair of branch lines 92C, 92D extends from the filter 112 to a drain filter line 114 connecting purified water line 92 to a drain line 116. Valves 118A, 118B within branch lines are provided to control the flow therethrough.

A drain line 122 extends from circulation conduit 42. A valve 124 is disposed in drain line 122 to control the flow of fluids from circulation conduit 42 to drain 116.

A plurality of storage tanks is provided for holding chemicals for use within washer 10. In the embodiment shown, three storage tanks, designated 142, 152, 162 are shown. Tanks 142, 152, 162 include feed lines 144, 154, 164, respectively, that connect storage tanks 142, 152, 162 to washing chamber 30. Pumps 146, 156, 166 are provided within feed lines 144, 154, 164 from storage tanks 142, 152, 162 to pump fluids (chemicals) from storage tanks 142, 152, 162 to washing chamber 30 for mixing with water therein. Pumps 146, 156, 166 are preferably metering pumps, wherein controlled amounts of chemicals can be introduced into washing chamber 30. In the embodiment shown, tank 142 contains an enzymatic cleaner, tank 152 contains a first part of a disinfectant and tank 162 contains a second part of a disinfectant. In the embodiment shown, flow meters 148, 158, 168 are provided in inlet lines 144, 154, 164, respectively, to monitor flow into washing chamber 30.

Figure 2:
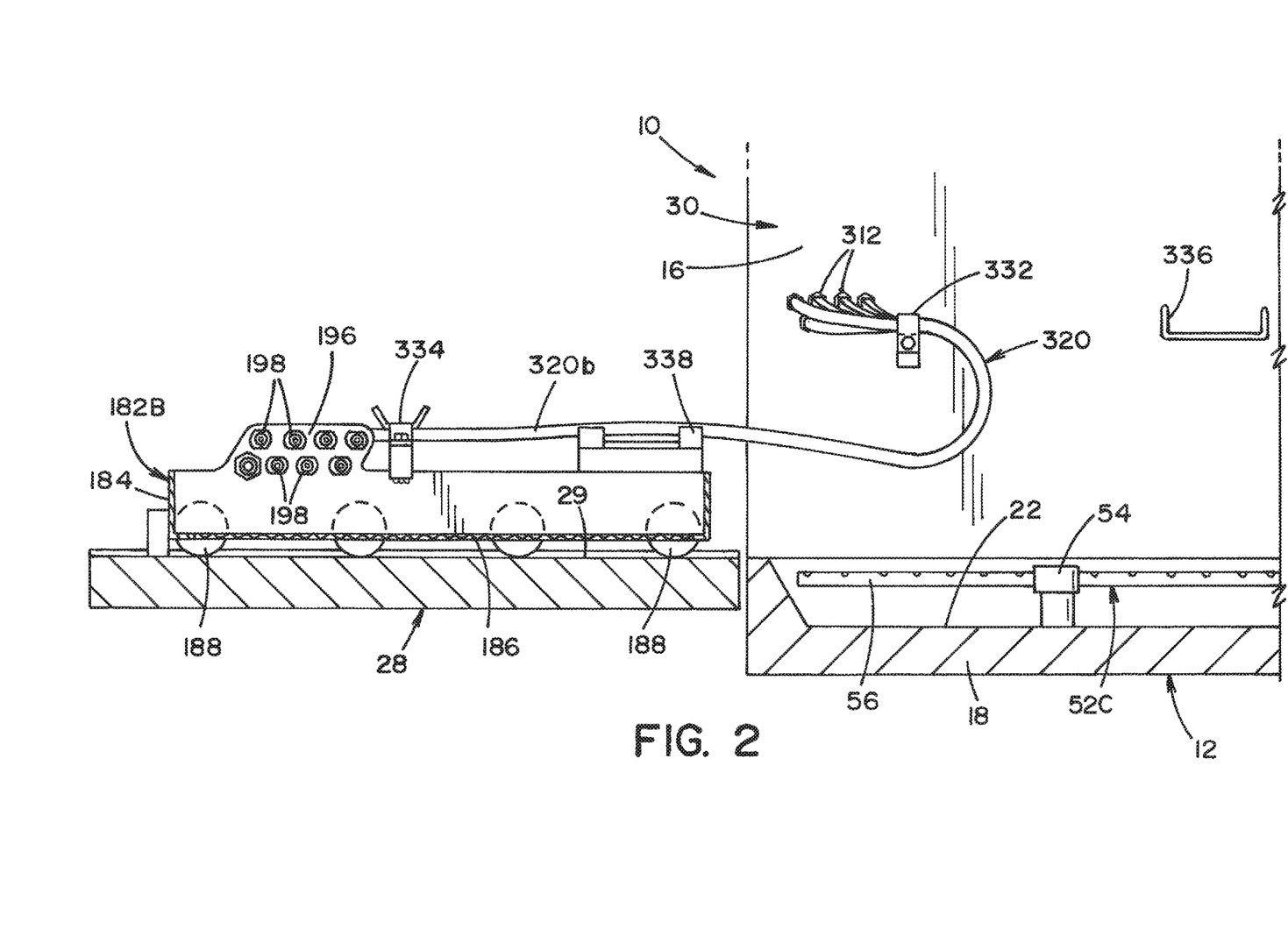
FIG. 2 is a side sectional view of the washing chamber and tray shown in FIG. 1, showing the tray (lower tray) removed from the washing chamber.
Figure 3:
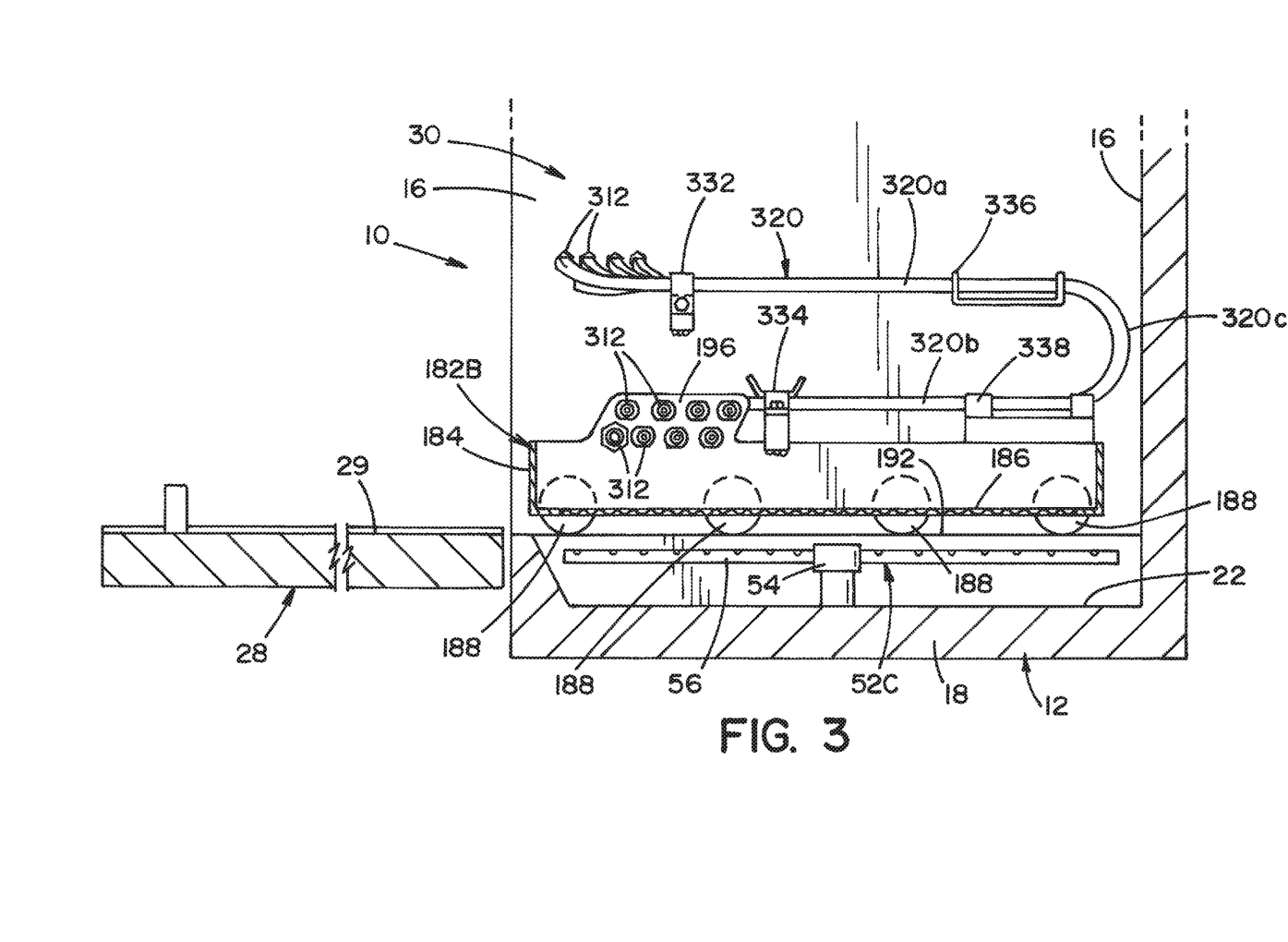
FIG. 3 is a side sectional view of the washing chamber shown in showing the tray inserted into the washing chamber.
Figure 4:
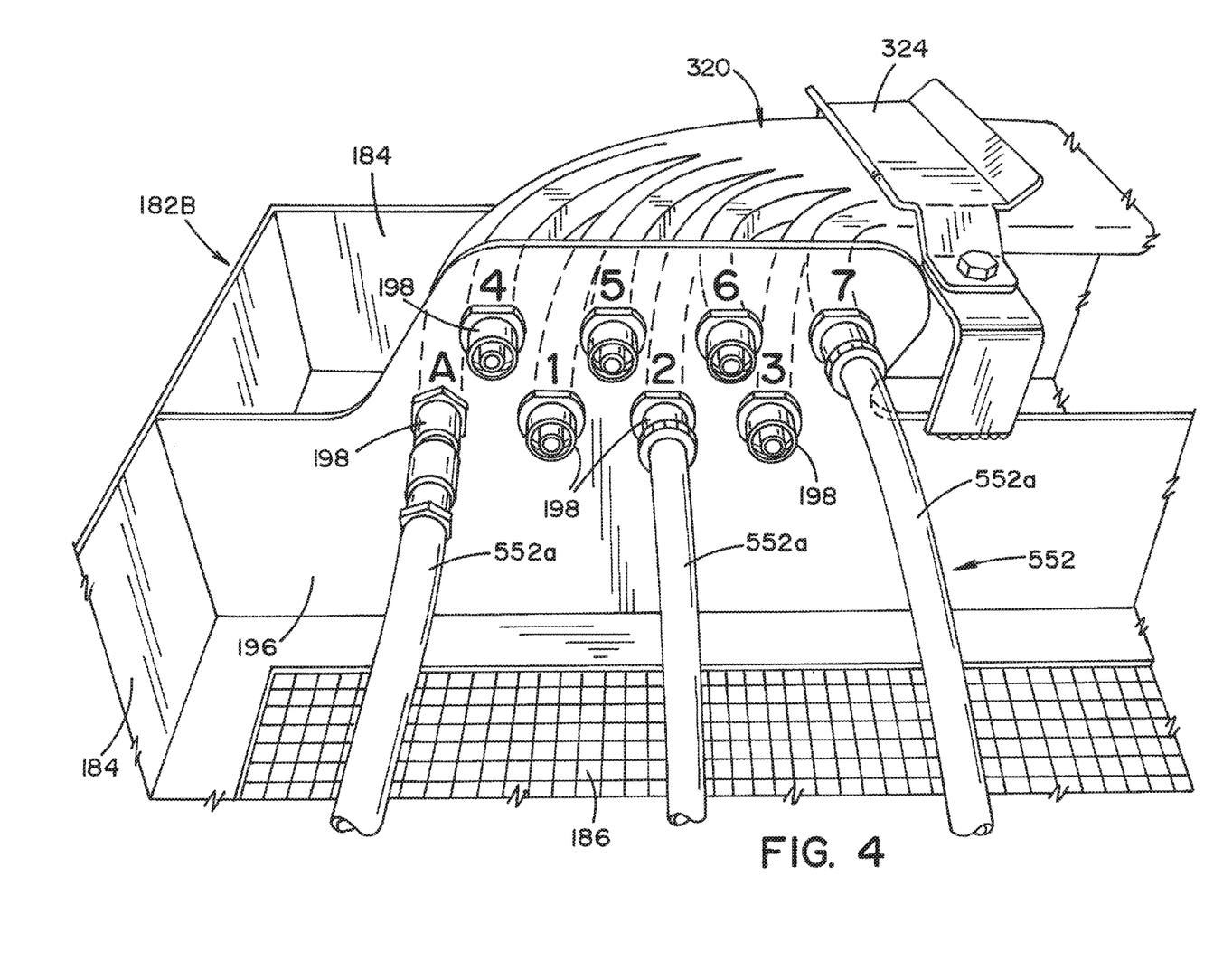
FIG. 4 is an enlarged perspective view of a mounting plate on the tray, showing one end of a flexible conduit attached to one side of the connecting plate and a plurality of connecting hoses attached to a second side of the connecting plate.

Washer 10 is dimensioned to contain one or more racks for holding medical instruments. In an embodiment shown, two (2) racks, i.e., an upper rack 182A and a lower rack 182B, are shown. Each rack 182A, 182B is dimensioned to hold an endoscope to be washed, as illustrated in FIG. 1. Upper rack 182A is dimensioned to be disposed between upper and intermediate spray arm assemblies 52A, 52B, and lower rack 182B is dimensioned to be disposed between intermediate and lower spray arm assemblies 52B, 52C. In the embodiment shown, each rack 182A, 182B, best seen in FIG. 1, is generally rectangular in shape and has an outer structural frame 184 and a porous bottom panel 186 formed of wire mesh or perforated metal that allows fluid to pass therethrough. Each rack 182A, 182B is movable between a first position within washing chamber 30 (as illustrated in FIG. 3) and a second position removed from washing chamber 30 (as best seen in FIGS. 1 and 2). Spaced apart rollers 188 are provided on opposite sides of frame 184 to allow a rack 182A, 182B to roll freely into and out of washing chamber 30 on tracks 192 formed along opposing side walls 16 of washing chamber 30, as is conventionally known. FIG. 2 shows door 28 in an open position with lower rack 182B removed from washing chamber 30. As illustrated, in FIG. 2, the inner surface of door 28 is formed to define a track 29 that is aligned with track 192 within washing chamber 30, when door 28 is in an opened position. A mounting plate 196 (best seen in FIGS. 1 and 4) is provided along one side of rack 182A, 182B. Mounting plate 196 supports a plurality of hose or tube connectors 198. One side of connectors 198 is adapted to be connected to one end of a flexible member 320 (that shall be described in greater detail below). The other side of connector 198 is for connection to a set of connecting hoses that are designed for connection to a specific type of endoscope (as will be described in greater detail below). In the embodiment shown, eight (8) connectors 198 are shown on mounting plate 196. One connector 198 is designated "A" on mounting plate 196 and the other seven connectors 198 are designated "1" through "7."

Washer 10 includes test system 200 for testing flow characteristic of channels (lumens) within an endoscope and for washing and cleaning the same. In the embodiment shown, test system 200 is comprised of two (2) test apparatus 210A, 210B. Each test apparatus 210A, 210B is of a type disclosed in U.S. Pat. No. 8,673,212 to MCDONNELL et al., the disclosure of which is expressly incorporated herein by reference. As best seen in FIG. 7, each test apparatus 210A, 210B is comprised of a manifold 212 defining an internal cavity (not shown). Manifold 212 includes a fluid inlet port 214 at one end and an air inlet port 216 at another end. In the embodiment shown, two test apparatuses 210A, 210B are connected in series with the internal cavity of apparatus 210A connected to internal cavity of apparatus 210B by a connection line 218. In this respect, in the embodiment shown, fluid inlet port 214 connected to manifold 212 of test apparatus 210B would communicate through connection line 218 to the internal cavity of manifold 212 of test apparatus 210A. Likewise, air inlet port 216 that communicates with the internal cavity of test apparatus 210A would communicate with the internal cavity of test apparatus 210B, as will be understood from a later explanation of the operation of the system.

Air inlet port 216 is connected to an air line 222 that connects manifold 212 of test apparatus 210A to a source of compressed air. The fluid inlet port and the air inlet port both communicate with the internal cavity within the manifold. A pressure regulator 224 is disposed in air line 222 to regulate the air pressure within air line 222. A valve 226 and flow meter 228 are disposed in air line 222 to monitor the amount of flow through air line 222. A directional check valve 232 and a second control valve 234 are disposed in air line 222 between flow meter 228 and test apparatus 210A.

Valve 234 controls flow to air inlet port 216. A pressure sensor 242 is provided in connection line 218 to detect pressure within manifold 212 of test apparatuses 210A, 210B. Air line 222 includes a branch line 222A that in turn splits into sub-branch lines 222B, 222C that connect to side wall 16 of washer 10. An air regulator 244 is disposed in branch line 222A to regulate the air pressure to sub-branch lines 222B, 222C. Control valves 252, 254 are disposed in sub-branch lines 222B, 222C, respectively, to control air flow therethrough. Pressure sensors 256, 258 are disposed in sub-branch lines 222B, 222C, respectively, to monitor the pressure therein.

A vent line 222D connects sub-branch line 222B to the external atmosphere. A control valve 262 controls venting of sub-branch line 222D. Similarly, a vent line 222E connects sub-branch line 222C to the external atmosphere. A control valve 264 is disposed in a vent line 222E to control venting of sub-branch line 222C.

Fluid inlet port 214 is connected to a fluid line 272 that is in fluid communication with circulation conduit 42. A control valve 274 is disposed in fluid line 272 to control flow to test system 200.

Referring now to test system 200, in the embodiment shown, washer 10 includes two (2) racks 182A, 182B, each rack for washing an endoscope. Accordingly, test system 200 includes two test apparatuses 210A, 210B, one apparatus to be associated with each endoscope to be cleaned. Test apparatuses 210A, 210B are essentially the same, and operate the same, and therefore only one test apparatus 210B shall be described in detail, it being understood that such description applies equally to test apparatus 210A. As best seen in FIG. 7, a plurality of outlet ports extends from manifold 212 of test apparatus 210B. In the embodiment shown, seven outlet ports, designated 280-1, 280-2, 280-3, 280-4, 280-5, 280-6, and 280-7, extend from manifold 212. Each outlet port 280-1, 280-2, 280-3, 280-4, 280-5, 280-6, 280-7 is connected to an outlet line 292 that connects to a connector 312 mounted to side wall 16 of washer 10. Connectors 312 are conventional hose or tube connectors that allow a fluid connection to be made through side wall 16. A control valve 294 is disposed in each outlet line 292 from outlet ports 280-1, 280-2, 280-3, 280-4, 280-5, 280-6, 280-7 from the manifold 212 to control flow therethrough.

Figure 5:
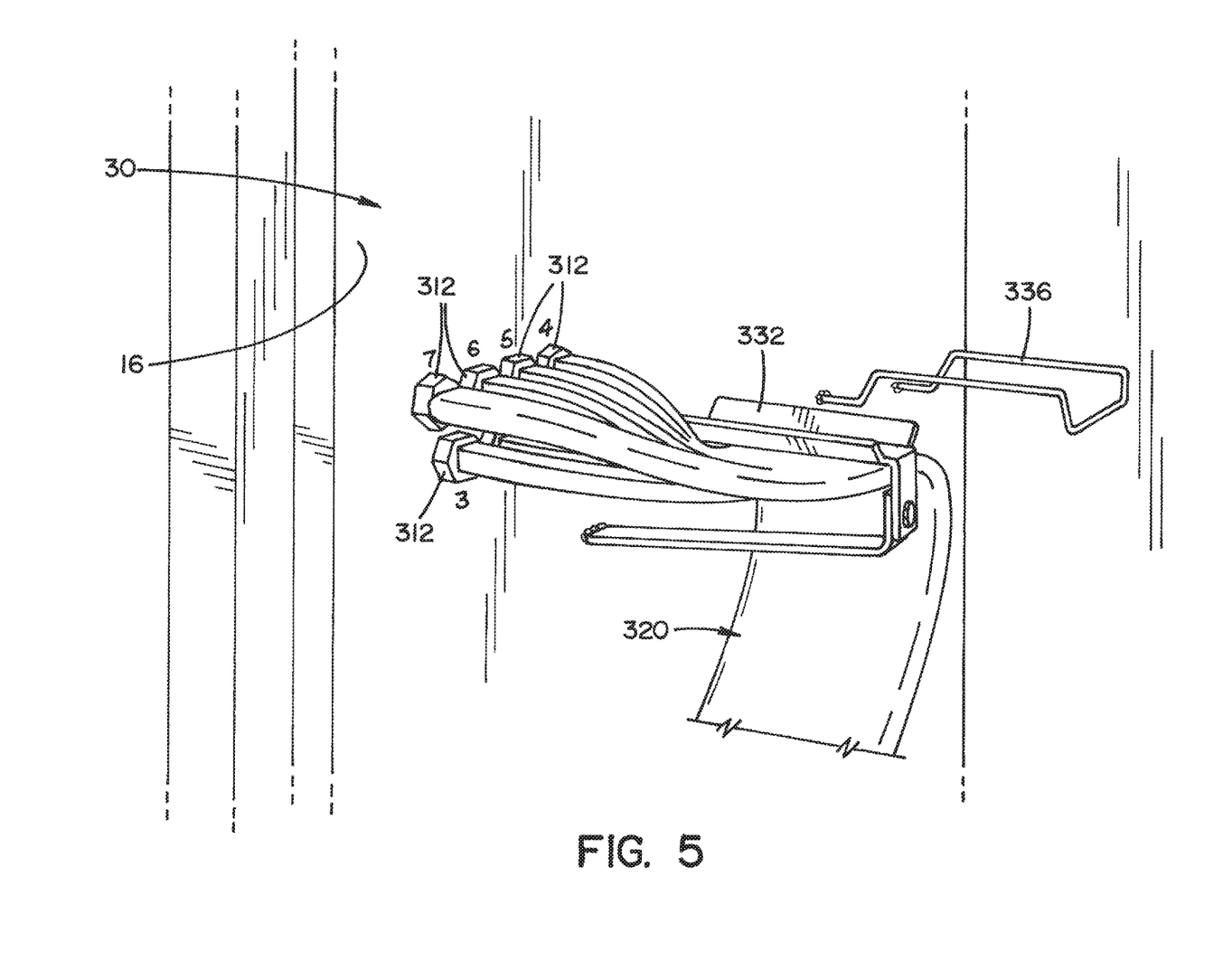
FIG. 5 is a perspective view of a side wall of the washing chamber, showing another end of the flexible cable connected to connectors extending through the side wall.

In accordance with one aspect of the present invention, an elongated flexible member 320 having a plurality of side by side passageways 322 formed therethrough are attached to connector 312 within washing chamber 30. Elongated flexible member 320 is basically a polymer extrusion wherein eight distinct passageways 322 are formed to extend parallel to each other in a common plane. In a preferred embodiment, flexible member 320 is formed of silicon. The ends of the flexible members 320 are splayed to separate each passageway 322 so as to allow connection of one end of flexible member 320 to connector 312 on side wall 16, as best seen in FIG. 5. In this respect, each outlet port 280-1, 280-2, 280-3, 280-4, 280-5, 280-6, 280-7 from manifold 212 is connected to a passageway 322 through flexible member 320 via an associated connection line 292. The other end of elongated flexible member 320 is connected to connector 198 on mounting plate 196 on a rack within washing chamber 30. Elongated flexible member 320 is basically a ribbon-like structure that is disposed within washing chamber 30 to replicate over itself as a rack 182A, 182B is moved within washer 10.

Figure 6:
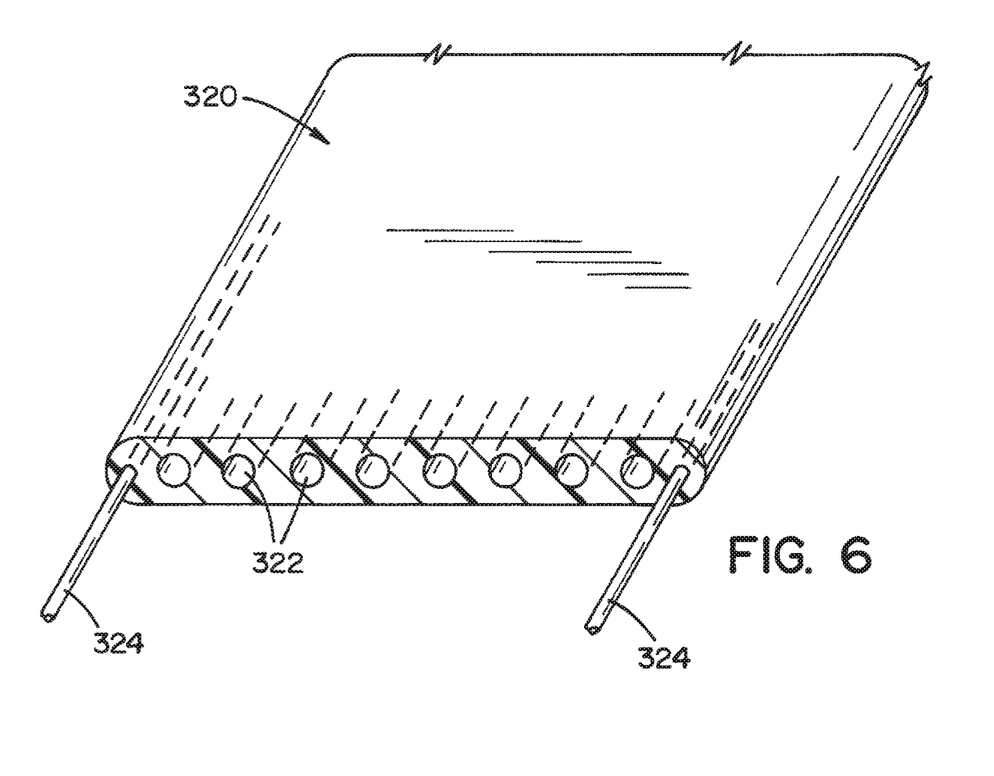
FIG. 6 is a cross-sectional view of the flexible connector showing a plurality of passageways extending therethrough and showing flexible rods embedded along the edges of the flexible connector.

In accordance with another aspect of the present invention, flexible member 320 is formed to include elongated flexible rods 324 (best seen in FIG. 6) extending along the lateral sides thereof. Elongated rods 324 are preferably formed of a spring-like, metal material having an original, normal, straight-line configuration. In this respect, when elongated flexible member 320 is replicated over itself, elongated rods 324 extending therethrough bias elongated member 320 to a generally flat, planar configuration. In the embodiment shown, elongated flexible member 320 has eight passageways 322 extending therethrough. As best seen in FIG. 5, a first bracket 332, attached to side wall 16 of washer 10 near connectors 312, captures and maintains the position of the first end of flexible member 320 relative to wall 16 of washer 10. A second bracket 334 attached to mounting plate 196 (best seen in FIG. 4) captures and maintains the position of the second end of flexible member 320 relative to rack 182B.

Flexible member 320 is connected to connectors 312 on side wall 16 and to connectors 198 on mounting plate 196 such that the connector 198 designated "A" on mounting plate 196 is fluidly connected to branch line 222C of air line 222, and connectors 198 designated "1, 2, 3, 4, 5, 6, and 7" on mounting plate 196 are fluidly connected respectively to outlet ports 280-1, 280-2, 280-3, 280-4, 280-5, 280-6, 280-7 on manifold 212.

As will be appreciated, the second end of elongated flexible member 320 moves with rack 182B as it moves from a position within the washing chamber 30 (FIG. 3) to a position outside washing chamber 30 (FIG. 2) and vice versa.

A guide/stop 336 is disposed along the inner surface of side wall 16 to guide and position a flexible member 320 when a rack 182A, 182B is positioned within washing chamber 30. As illustrated in FIG. 3, that shows lower rack 182B within washing chamber 30, guide/stop 336 causes flexible member 320 to assume a generally U-shaped configuration, when rack 182B is within washing chamber 30. In this configuration, flexible member 320 has a first, generally straight section 320a above a second, generally straight section 320b. In this respect, elongated rods 324 embedded in flexible member 320 help align first and second sections 320a, 320b into generally straight configurations. A curved section 320c connects first section 320a to section 320b. Guide/stop 336 is preferably positioned relative to connectors 312 to slope first section 320a downward toward curved section 320c. Similarly, a holder 338 on tray 1829 slightly slopes section 320b toward connectors 198. In this respect, flexible member 320 preferably slopes continuously downward from connector 312 to connector 198 to facilitate draining of passageways 322 in flexible member 320.

A controller 400 is provided to monitor and control the operation of testing system 200, as well as washer 10. In this respect, all the pressure sensors and the flow measuring devices within washer 10 and test system 200 are connected to controller 400. Controller 400 monitors signals from the pressure sensors as well as flow through the various sections of air inlet line 222. Pressure sensor 242 connected to manifold 212 provides signals to controller 400 with respect to the pressure within manifolds 212. Controller 400 likewise controls all control valves within air inlet line 222 as well as the control valves in circulation system 40. In addition, controller 400 controls each of control valves 294 associated with outlet ports from module 212 wherein flow through each of outlet lines 292 can be individually controlled.

Referring now to the operation of the system 10, as indicated above, there are typically hundreds of known endoscopes, each having its own internal configuration with passageways. The present invention allows connection to an endoscope (designated "ES" in the drawings) with up to seven internal passageways.

Set-Up Procedure

Prior to washing endoscopes ES within washer/disinfector 10, a set-up procedure is performed to establish baseline operating characteristics for each endoscope ES to be cleaned within washer/disinfector 10. In this respect, as indicated above, many different types of endoscopes ES exist, and each has a particular internal configuration with respect to the number and shape of lumens therein. Prior to actually washing endoscopes ES within washers/disinfector 10, a clean endoscope ES is attached to a test apparatus 210A or 2109 via connection lines 292 and flexible member 320 within washer/disinfector 10. A "characterization test" is then performed on the endoscope ES to establish baseline operating characteristics for a clean endoscope ES of that type. More specifically, three tests are performed on each endoscope ES to provide specific information regarding the operating characteristics of the endoscope ES. First, the flow characteristics of the endoscope ES (and the lumens therein)

are established. Specifically, a flow coefficient ($C_v$) is established for each channel or lumen in the endoscope ES by performing an air pressure/flow test thereon.

Specifically, pressurized air is applied to each lumen of the endoscope ES by allowing air at a set pressure to flow through manifold 212 and connection line 292. Flow through the lumen at an established pressure is monitored by flow meter 220. A flow coefficient ($C_v$) is calculated for each lumen in the endoscope ES based upon the air flow at the given pressure.

Knowing the flow coefficient for each lumen of a clean endoscope ES, the controller then calculates and stores a "blockage value" or "blockage threshold value" that is used to determine whether or not a lumen is suitable for cleaning. This "threshold value" is determined as a percentage of flow of a clean lumen. In a preferred embodiment, controller 400 is programmed to set 30% to 40% blockage as a value above which the lumen is not suitable for cleaning. In other words, if 40% blockage is set as the blockage threshold value, a lumen is suitable for cleaning if 60% or more of the original flow value of the lumen exists. These values for each of the lumens for a particular endoscope ES are stored in controller 400.

After determining a "blockage threshold value" for each of the lumens in the endoscope ES, a second test is performed wherein, each connection to the endoscope ES is disconnected, and pressurized air is applied through the test apparatus to determine air flow through each of connection lines 292. This value is also stored in memory in controller 400 with respect to the tested endoscope ES. Thus, according to the present invention, a threshold flow value and a disconnect flow value is determined and stored in controller 400 for each lumen in each endoscope ES.

Lastly, a third test is performed to determine the configuration of lumens within the endoscope namely whether two or more lumens merge into a single lumen or channel within the endoscope ES. In accordance with another aspect of the present invention, following the initial test to determine a flow coefficient ($C_v$) for each of the lumens within the clean endoscope ES, each possible pair of lumens within the endoscope ES is tested together under the set pressure to determine a "pair flow coefficient ($C_v$-pair)" for the selected pair of lumens. The pair flow coefficient ($C_v$-pair) for the pair is then compared to the sum of the individual flow coefficients of the two lumens that make up the pair. In other words, two lumens in the endoscope ES are tested together and a pair flow coefficient ($C_v$-pair) for the pair of lumens is established. This pair flow coefficient ($C_v$-pair) is compared to the sum of the separate flow coefficients ($C_v$) of the two lumens. If both values are equal, this is an indication that the two lumens are separate. If, however, a lower flow coefficient is established for the pair flow coefficient ($C_v$-pair) of the two lumens as compared to the sum of the individual flow coefficients ($C_v$) of the two lumens, this is an indication that the two lumens merge into a single lumen within the endoscope ES. In this respect, as indicated above, in some endoscopes ES, two passageways (lumens) merge into a single passageway within the endoscope. The ability to determine when pairs of lumens merge into a single lumen is important when purging fluid from combined lumens, as shall be described in greater detail below. Flow characteristics of any merged or joined lumens are stored in memory in controller 400.

According to another aspect of the present invention, purge times for each of the channels (lumens) within an endoscope ES are determined based upon the flow coefficient values ($C_v$) determined during the flow/check at the beginning of set-up cycle. In other words, once the flow coefficient ($C_v$) for each of the lumens or for each joined pair of lumens is determined, a purge time sufficient to purge fluid from the lumen is calculated. If channels within the endoscope are found to be merged (as indicated above), the purge time is then the sum of all purge times of all of the merged channels. It has been found that the time necessary to purge a lumen can be determined based upon its flow coefficient. Specifically, the purge time (in seconds)= $52500 \cdot C_v^{-1.15} + 2$. This relationship is determined based upon the dimension of a particular lumen, as well as the flow characteristics of the lumen at a given point in time. This calculation determines the time to clear liquid from lumen based upon the flow characteristics of the lumen.

The foregoing tests and calculations are performed for each lumen or channel in each type or model of endoscope ES to be cleaned within washer/disinfector 10 to establish 1) a threshold blockage value that would indicate whether the endoscope ES is suitable for cleaning, 2) a disconnect value indicative of an improper connection, and 3) flow values indicating merged or joined lumens or channels within an endoscope ES. This data is stored in memory in controller 400 for each endoscope ES to be washed within washer/disinfector 10. Each endoscope ES can be identified in controller 400 by a customer number or by a serial number on the endoscope ES. Thus, a directory of different types of endoscopes ES to be cleaned is stored within controller 400 for use during a washing cycle.

For a given type or model of endoscope ES, a set 522 of connecting tubes 522a (best seen in FIG. 1) are provided to connect specific ports on the endoscope ES to specific connectors 198 on mounting plate 196. Connection tubes 522a are then connected to the endoscope ES and to respective connectors 198 on the mounting plate 196 of rack 182B, rack 182B, with the endoscope ES thereon, is slid into washing chamber 30 and the door to washing chamber 30 is closed. An operator then initiates a washing cycle.

Washing/Disinfection Cycle

A preferred washing/disinfection cycle, in accordance with one aspect of the present invention, includes a first endoscope check phase, a pre-wash phase, a wash phase, a first rinse phase, a chemical disinfection phase, a final air phase, and a second endoscope ES check phase. As will be appreciated, the pre-wash phase, wash phase, rinse phases and chemical disinfection phases all involve use of a liquid. Following each of these phases, the liquid within the lumens of the endoscope ES are purged from the lumens prior to a subsequent operational phase, as shall be described in greater detail below.

During the endoscope check phase, pressurized air is applied to each lumen of the endoscope ES by allowing air at a set pressure to flow through manifold 212, connection line 292 and flexible member 320. The flow through each lumen is detected by flow meter 228 that sends signal to controller 400.

Flow through each lumen in the endoscope ES is determined and compared by controller 400, the "threshold flow value" and "disconnected flow value" stored in memory. A flow value too low (i.e., below the "threshold flow value") indicates a lumen is obstructed and not suitable for cleaning. A flow value too high (i.e., at or above the "disconnect flow value") for a lumen indicates that the lumen is improperly connected or not connected, and therefore not suitable for cleaning. In this respect, a flow value between the "threshold flow value" and the "disconnect flow value" indicates a lumen is suitable for cleaning.

If a lumen does not meet the "threshold flow value," according to another aspect of the present invention, a purge is performed on the obstructed lumen. The purge involves blowing pressurized air through the lumen for a predetermined period of time. Thereafter, the flow value through the lumen is retested. If the lumen is still determined to be obstructed (i.e., the flow through the lumen does not meet the threshold value), controller 400 provides an indication to the user, by either audio or visual indication, that a lumen within the endoscope ES is blocked and the endoscope ES cannot be reprocessed. The user may be prompted or instructed that the endoscope ES requires manual cleaning prior to washing/disinfecting in washer/disinfector 10.

If the endoscope ES meets the conditions for washing, a pre-wash phase is initiated. During the pre-wash phase, non-heated cold water is introduced into washer 10 by controller 400 opening valve 84. The cold water is collected in sump 22 and conveyed by pump 62 to spray assemblies 52A, 52B, 52C within the washer 10 to wash the exterior of the endoscope ES. The cold water is also conveyed to manifold 212 and to lumens within the endoscope ES to pre-wash the interior of each of the lumens. Pre-wash is conducted for a predetermined period of time. Following the pre-wash, each of the lumens is purged by directing compressed air from air line 222 through manifold 212 to each of the lumens (passageways) within the endoscope During the purge phase, each lumen is exposed to pressurized air to force the pre-wash fluid within the lumens out thereof. Since a purge time has been established for each of the lumens, air pressure is maintained on each of the lumens for the select purge time for each lumen. Once the purge time for a particular lumen has elapsed, closing control valve 294 associated with the lumen shuts off further flow of compressed air to the lumen. As will be appreciated by one skilled in the art, the lumens within an endoscope ES vary in length, as well as diameter. Longer lumens with large diameter passageways contain significantly more fluid than smaller, shorter lumens with smaller inner diameters. Thus, the time to purge these different types of lumens could vary significantly. In accordance with the present invention, once the calculated purge time for a particular lumen has been reached, control valve 294 to the specific lumen is shut, thereby preventing further air from being forced through the already-purged lumen. In this respect, once a calculated purge time for a particular lumen is reached, the associated control valve 294 is closed to maintain a maximum pressure at the inlets of other channels still being purged. As will be appreciated, the purge cycle to purge the entire endoscope ES is the purge time for the particular lumen having the longest purge time.

Once the purge cycle phase been completed, a wash phase is initiated. The wash phase consists of introducing heated and cold water into washer 10 through hot water line 72. Washing chemicals are introduced into washing chamber 30 from tanks 142, 152, or 162. A washing fluid is pumped by pump 62 to spray assemblies 52A, 52B, 52C and to manifold 212 from which the washing fluid is directed into each of the lumens of the endoscope ES. The wash fluid flows through each lumen (i.e., through the endoscope ES) for a predetermined period of time, such that each lumen is exposed to the washing fluid for a minimum predetermined time necessary to wash the lumen.

Following the wash cycle, the lumens are purged of washing fluid by conducting another purge cycle, as described above. As indicated above, the purge cycle is based upon the flow coefficient ($C_v$) established during the endoscope ES check phase of the overall reprocessing cycle.

As noted above, one aspect of the present invention is the ability to detect passageways (lumens) that merge within the endoscope ES. The purge time for such combined channels is the purge time determined for each individual channel. In this respect, the combined channels are also purged together rather than independently to avoid the problem of fluid being forced back up one branch of the combined channels, which might occur if one channel were purged separately. By purging the two channels together for a prolonged period of time, it insures that all of the fluids within the channels that merge are purged from the endoscope ES.

Following the purge phase to remove washing fluid from the endoscope ES, a rinse phase is initiated. Non-heated cold water is circulated through washing chamber 30, sprayed onto the exterior of the endoscope ES and forced through manifold 212 through the lumens of the endoscope ES.

Following the first rinse phase, the lumens of the endoscope ES are purged of the rinse water in a manner as described above. Following this purge phase, the endoscope ES is exposed to a chemical disinfectant by introducing a chemical disinfectant and water to washing chamber 30. The chemical disinfectant is circulated through the circulation system to spray assemblies 52A, 52B, 52C onto the exterior of the endoscopes ES, and circulated through manifold 212 to the passageways (lumens) of the endoscope ES. The chemical disinfectant is circulated through the circulation system and through the lumens for a predetermined period of time, wherein each lumen has a minimum exposure time to the chemical disinfectant.

Following the chemical disinfection, the lumens are again purged of fluid for a predetermined period of time, as described above. Following the chemical disinfection, a second rinse phase is initiated to rinse the exterior of the endoscope ES and the passageways within the endoscope ES with clean filtered rinse water. A third rinse phase is then conducted with clean filtered rinse water to further rinse any chemical disinfectant from the exterior and interior passageways (lumens) through the endoscope ES.

Following the third rinse, a final air purge phase is initiated to purge the lumens of any rinse water within the endoscope ES. The final air purge may extend for a duration longer than the previous purge phases to insure near drying of the endoscope ES.

Following the final air purge, a second endoscope ES check phase test is conducted. This second endoscope ES test phase tests the flow characteristics of each of the passageways (lumens) within the endoscope ES by monitoring the air pressure and air flow individually through each of the lumens.

The present invention thus provides a method of cleaning passageways (lumens) within an endoscope that automates the cycle times and purge times of the washing of the lumens based upon initial flow characteristics determined at the beginning of a reprocessing cycle. In addition, the present invention provides a method of determining which passageways within an endoscope may merge into a single passageway within the endoscope, thereby insuring proper cleaning and purging of the endoscope during the respective phases of the overall washing cycle.

Having described the invention, the following is claimed:
1. A method for operating a computer-controlled washer/disinfector for cleaning a medical endoscope, said method comprising the steps of:
    storing in memory identification and operating characteristics for a plurality of clean endoscopes, said operating characteristics including flow characteristics for each lumen within an endoscope and a blockage threshold flow coefficient for each lumen within an endoscope;
connecting each lumen of an endoscope to be cleaned to a fluid distribution system for selectively conveying pressurized air or pressurized fluids through lumens in an endoscope;
identifying the type of endoscope to be cleaned in said washer/disinfector;
determining said blockage threshold flow coefficient for each lumen for said endoscope to be cleaned;
pressurizing each lumen in said endoscope individually and determining an actual flow coefficient through said lumen, wherein determining the actual flow coefficient includes determining an actual flow coefficient value (Cv) for each lumen within the endoscope and a purge time to purge fluid from a lumen based upon its flow coefficient value (Cv);
determining whether said endoscope is suitable for cleaning by comparing said actual flow coefficients for a lumen in said endoscope to said blockage threshold flow coefficient for said lumen; and
determining whether a connection to a lumen in said endoscope is properly connected based upon said flow coefficient through said lumen.

2. A method for operating a computer-controlled washer/disinfector as claimed in claim 1, further comprising the step of initiating a washing/decontaminating cycle if each of the actual flow coefficients of said lumens in said endoscope exceeds said blockage threshold flow coefficients.

3. A method for operating a computer-controlled washer/disinfector as claimed in claim 1, further comprising the step of preventing initiation of a washing/decontaminating cycle if one of the actual flow coefficients of said lumen in said endoscope is below said blockage threshold flow coefficient.

4. A method of operating a computer-controlled washer/disinfector as described in claim 1, wherein said washing/disinfecting cycle includes a pre-wash phase, a wash phase, a first rinse phase, and a chemical disinfection phase.

5. A method of operating a computer-controlled washer/disinfector as described in claim 4, wherein a purge phase is performed between each phase of said washing/disinfecting cycle that includes a liquid.

6. A method of operating a computer-controlled washer/disinfector as described in claim 1, wherein said purge time (in seconds) equals $52500 \cdot Cv^{-1.15} + 2$.

7. A method of operating a computer-controlled washer/disinfector as described in claim 1, wherein an actual flow coefficient through a lumen that is below the threshold flow coefficient indicates a lumen is obstructed and not suitable for cleaning.

8. A method of operating a computer-controlled washer/disinfector as described in claim 1, wherein an actual flow coefficient through a lumen that is above a "disconnect flow coefficient" indicates that a lumen is improperly connected or not connected and not suitable for cleaning.

9. A method for operating a computer-controlled washer/disinfector for cleaning a medical endoscope, said method comprising the steps of:
storing in memory identification and operating characteristics for a plurality of clean endoscopes, said operating characteristics including flow characteristics for each lumen within an endoscope and a blockage threshold flow coefficient for each lumen within an endoscope;
connecting each lumen of an endoscope to be cleaned to a fluid distribution system for selectively conveying pressurized air or pressurized fluids through lumens in an endoscope;
identifying the type of endoscope to be cleaned in said washer/disinfector;
determining said blockage threshold flow coefficient for each lumen for said endoscope to be cleaned;
pressurizing each lumen in said endoscope individually and determining an actual flow coefficient through said lumen;
determining whether said endoscope is suitable for cleaning by comparing said actual flow coefficients for a lumen in said endoscope to said blockage threshold flow coefficient for said lumen;
determining whether a connection to a lumen in said endoscope is properly connected based upon said flow coefficient through said lumen; and
determining if two lumens merge into a single lumen within said endoscope by:
determining an individual air flow coefficient for each of two lumens in said endoscope;
determining a combined air flow for said two lumens in said endoscope; and
comparing the air flow coefficient for said two lumens to a sum of the individual air flow coefficients of said two lumens.

10. A method of testing channels or lumens within an endoscope, comprising the steps of:
a) connecting each individual lumen within an endo scope to a source of pressure;
b) measuring the pressure and air flow through each individual lumen separately;
c) determining a flow coefficient for each individual lumen based on said measured air pressure and said measured air flow;
d) exposing each possible pair of lumens in said endoscope to said source of pressure;
e) determining a flow coefficient for said each possible pair of lumens in said endoscope based on a measured air flow at a measured pressure for said pair of lumens; and
f) comparing the flow coefficient for a pair of lumens to a sum of the flow coefficients of the individual lumens forming said pair of lumens, wherein a flow coefficient for said pair of lumens that is less than the sum of the air flow coefficients of the individual lumens forming said pair is indicative of said pair of lumens merging into a single lumen within said endoscope.

11. A method of testing channels or lumens within an endoscope as described in claim 10, wherein cleaning and purging of said merged lumens is based upon said flow coefficient for said pair of lumens.

12. A method of testing channels or lumens within an endoscope as described in claim 1, wherein determining said blockage threshold flow coefficient for each lumen for said endoscope to be cleaned includes determining said blockage threshold flow coefficient based on the identified type of endoscope and the identification and operating characteristics stored in memory.

13. A method of testing channels or lumens within an endoscope as described in claim 1, wherein storing in memory identification and operating characteristics comprises storing at least one of a customer number or a serial number on the endoscope.

14. A method of testing channels or lumens within an endoscope as described in claim 13, wherein identifying the type of endoscope comprises using the at least one of the customer number or the serial number to identify the type of endoscope.

* * * * *